US009370608B2

(12) United States Patent
Lamberti et al.

(10) Patent No.: US 9,370,608 B2
(45) Date of Patent: Jun. 21, 2016

(54) CONTINUOUS MATRIX WITH OSTEOCONDUCTIVE PARTICLES DISPERSED THEREIN, METHOD OF FORMING THEREOF, AND METHOD OF REGENERATING BONE THEREWITH

(71) Applicant: PIONEER SURGICAL TECHNOLOGY, Marquette, MI (US)

(72) Inventors: Francis Vincent Lamberti, Cary, NC (US); Ronald Stewart Hill, Greenville, NC (US); Adam MacMillan, Quincy, MA (US); Edward Ahn, Dover, MA (US); Brian Schlossberg, Chestnut Hill, MA (US); Stephen Capistron, Melrose, MA (US); William H. Lloyd, Winterville, NC (US)

(73) Assignee: RTI Surgical Inc., Marquette, MI (US)

( * ) Notice: Subject to any disclaimer, the term of this patent is extended or adjusted under 35 U.S.C. 154(b) by 0 days.

(21) Appl. No.: 14/568,339

(22) Filed: Dec. 12, 2014

(65) Prior Publication Data

US 2015/0098998 A1 Apr. 9, 2015

Related U.S. Application Data

(63) Continuation of application No. 13/722,237, filed on Dec. 20, 2012, now Pat. No. 8,940,317.

(60) Provisional application No. 61/579,820, filed on Dec. 23, 2011.

(51) Int. Cl.
| | |
|---|---|
| *A61F 2/28* | (2006.01) |
| *A61L 27/46* | (2006.01) |
| *A61K 9/00* | (2006.01) |
| *A61L 27/54* | (2006.01) |
| *A61L 27/58* | (2006.01) |
| *C08L 89/00* | (2006.01) |
| *A61L 27/48* | (2006.01) |
| *A61L 27/22* | (2006.01) |
| *A61L 27/40* | (2006.01) |
| *A61L 27/56* | (2006.01) |

(52) U.S. Cl.
CPC .............. *A61L 27/46* (2013.01); *A61K 9/0024* (2013.01); *A61L 27/22* (2013.01); *A61L 27/40* (2013.01); *A61L 27/48* (2013.01); *A61L 27/54* (2013.01); *A61L 27/56* (2013.01); *A61L 27/58* (2013.01); *C08L 89/00* (2013.01); *A61L 2300/112* (2013.01); *A61L 2400/06* (2013.01); *A61L 2430/02* (2013.01)

(58) Field of Classification Search
CPC ...... A61K 9/0024; A61K 27/54; A61K 27/58
See application file for complete search history.

(56) References Cited

U.S. PATENT DOCUMENTS

| | | | |
|---|---|---|---|
| 5,470,911 A | 11/1995 | Rhee et al. | |
| 5,514,379 A | 5/1996 | Weissleder et al. | |
| 5,614,205 A | 3/1997 | Usala | |
| 5,776,324 A | 7/1998 | Usala | |
| 5,824,331 A | 10/1998 | Usala | |
| 5,830,492 A | 11/1998 | Usala | |
| 5,834,005 A | 11/1998 | Usala | |
| 5,908,633 A | 6/1999 | Usala | |
| 5,922,339 A | 7/1999 | Usala | |
| 5,972,385 A | 10/1999 | Liu et al. | |
| 6,113,629 A | 9/2000 | Ken | |
| 6,132,759 A | 10/2000 | Schacht et al. | |
| 6,231,881 B1 | 5/2001 | Usala et al. | |
| 6,261,587 B1 | 7/2001 | Usala | |
| 6,264,992 B1 | 7/2001 | Voytik-Harbin et al. | |
| 6,299,448 B1 | 10/2001 | Zdrahala et al. | |
| 6,315,994 B2 | 11/2001 | Usala et al. | |
| 6,352,707 B1 | 3/2002 | Usala | |
| 6,471,993 B1 | 10/2002 | Shastri et al. | |
| 6,713,079 B2 | 3/2004 | Usala | |
| 6,730,315 B2 | 5/2004 | Usala et al. | |
| 6,992,062 B2 | 1/2006 | Usala | |
| 7,303,814 B2 | 12/2007 | Lamberti et al. | |
| 7,700,660 B2 | 4/2010 | Usala | |
| 7,799,767 B2 | 9/2010 | Lamberti et al. | |
| 7,947,759 B2 | 5/2011 | Lin et al. | |
| 8,029,755 B2 | 10/2011 | Ahn | |
| RE43,661 E | 9/2012 | Ying et al. | |
| 2001/0033834 A1 | 10/2001 | Wilkison et al. | |

(Continued)

FOREIGN PATENT DOCUMENTS

WO WO 03/072155 9/2003

OTHER PUBLICATIONS

Aso et al., "Thermally Controlled Protein Release From Geltain-Dextran Hydrogels," *Radiation Physics and Chemistry*, 1999, pp. 179-183, vol. 55.

Chen et al., "Novel Glycidyl Methacrylated Dextran (Dex-GMA)/Gelatin Hdrogel Scaffolds Containing Microspheres Loaded with Bone Morphogenetic Proteins: Formulation and Characteristics," *Journal of Controlled Release*, 2011, pp. 65-77, vol. 118.

Chen et al., "Periodontal Regeneration Using Novel Glycidyl Methacrylated Dextran (Dex-GMA)/Gelatin Scaffolds Containing Microspheres Loaded with Bone Morphogenetic Proteins," *Journal of Controlled Release*, 2007, pp. 81-90, vol. 121.

Drury et al. "Hydrogels for Tissue Engineering: Scaffold Design Variables and Applications," *Biomaterials*, 2003, pp. 4337-4351, vol. 24.

Hoffman, "Hydrogels for Biomedical Applications," *Advanced Drug Delivery*, 2002, pp. 3-12, vol. 43.

(Continued)

*Primary Examiner* — Carlos Azpuru

(74) *Attorney, Agent, or Firm* — Womble Carlyle Sandridge & Rice, LLP

(57) ABSTRACT

The present disclosure provides compositions useful in regeneration of connective tissue, particularly bone. The compositions comprise a continuous matrix formed of a polypeptide crosslinked with a second polymer and further comprise particles of a porous, osteoconductive material dispersed in the continuous matrix. The composition can be provided in a dehydrated form. The disclosure further provides methods of preparing the composition in a clinically useful form, methods of using the composition in regenerating bone, and kits including the composition.

26 Claims, No Drawings

(56) References Cited

U.S. PATENT DOCUMENTS

| | | |
|---|---|---|
| 2002/0169120 A1 | 11/2002 | Blanchat et al. |
| 2002/0169201 A1 | 11/2002 | Falchuk |
| 2002/0176893 A1 | 11/2002 | Wironen et al. |
| 2002/0192263 A1 | 12/2002 | Merboth et al. |
| 2003/0032098 A1 | 2/2003 | Young et al. |
| 2003/0147935 A1 | 8/2003 | Binette et al. |
| 2003/0220245 A1 | 11/2003 | Hubbell et al. |
| 2004/0091462 A1 | 5/2004 | Lin et al. |
| 2004/0117033 A1 | 6/2004 | Frondoza et al. |
| 2004/0138128 A1 | 7/2004 | Lee et al. |
| 2004/0170663 A1 | 9/2004 | Wang et al. |
| 2005/0118230 A1 | 6/2005 | Hill et al. |
| 2005/0176620 A1 | 8/2005 | Prestwich et al. |
| 2007/0248685 A1 | 10/2007 | Qian et al. |
| 2009/0130756 A1 | 5/2009 | Klann et al. |
| 2011/0004307 A1 | 1/2011 | Ahn et al. |

OTHER PUBLICATIONS

Jennings, "Effect of Formulation on Lyophilization, Part 1" *IVD Technology*, 1997, pp. 1-6. http://www.ivdtechnology.com/print/1212.

Liu et al., "Covalent Bonding of PMMA, PBMA, and poly(HEMA) to Hydroxyapatite Particles," *J. Biomed Mater Res*, 1998, pp. 257-263, vol. 40.

Noro et al., "Biochemical Behavior of Hydroxyapatite as Bone Substitute Material in a Loaded Implant Model, on the Suface Strain Measurement and the Maximum Compression Strength Determination of Material Crash" *Biomedical Materials and Engineering*, 1999, pp. 319-324, vol. 9.

Wells, "Additivity of Mutational Effects in Proteins," *Biochemistry*, 1990, pp. 8509-8517, vol. 29, No. 37.

Zhang et al., "Inverted-Colloidal-Crystal Hydrogel Matrices as Three-Dimensional Cell Scaffolds," *Advanced Functional Materials*, 2005, pp. 725-731, vol. 15, No. 5.

CONTINUOUS MATRIX WITH OSTEOCONDUCTIVE PARTICLES DISPERSED THEREIN, METHOD OF FORMING THEREOF, AND METHOD OF REGENERATING BONE THEREWITH

CROSS-REFERENCE TO RELATED APPLICATIONS

The present application is a division of U.S. patent application Ser. No. 13/722,237, filed Dec. 20, 2012, the disclosure of which is incorporated herein by reference in its entirety.

FIELD OF THE DISCLOSURE

The present disclosure relates to a continuous matrix formed of a first biocompatible polymer crosslinked with a second biocompatible polymer, the matrix having dispersed therein particles of a porous, osteoconductive material, at least a portion of the pores of the particles having adsorbed therein a biocompatible material. The disclosure further relates to methods of preparing such matrices and methods of using such matrices.

BACKGROUND OF THE DISCLOSURE

Successful growth of bone in voids or gaps, either surgically created or arising from disease or injury, is an ongoing challenge. Many techniques have been used in an attempt to enhance bone growth, and several bone filler materials are commercially available. Nevertheless, there remains a need for bone filler compositions in a form that provides for good shelf life, is easy to use, and is effective across a variety of uses.

BRIEF SUMMARY OF THE DISCLOSURE

The present disclosure provides an osteoconductive, resorbable bone filler composition formed of a continuous matrix of a crosslinked hydrogel with particles of a porous, osteoconductive material dispersed therein. The composition can be provided in a dehydrated state and can be formed into desirable shapes. Moreover, the dehydrated composition can be cut or otherwise shaped as required at the time of use. When rehydrated, the matrix can conform to the anatomy of the treatment site.

The composition can be used for regenerating bone in a variety of applications and may particularly be used for filling bone defects. Such defects in the bone may be surgically created osseous defects or may be defects created from traumatic injury to the bone or from disease. The composition can be packed into bony voids or gaps and can be hydrated at the time of use (e.g., rehydrated from a dehydrated form at the time of use) or can be hydrated in vivo. The composition beneficially resorbs and is replaced by the growth of new bone during the healing process. In specific embodiments, the composition can be particularly useful in spinal applications, such as posterolateral spinal fusion procedures and for packing into interbody cages within the spinal column. The dehydrated material can be rehydrated using a variety of materials, including sterile water, buffer solution, and natural body fluids, including bone marrow aspirates. If desired, the composition can be combined with further materials, such as autogenous bone and osteoinductive materials.

In certain embodiments, the disclosure thus provides a composition comprising: a continuous matrix formed of a polypeptide (i.e., a "first polymer") crosslinked with a second polymer, such as a polysaccharide or a synthetic polymer; and particles of a porous, osteoconductive material dispersed in the continuous matrix; wherein the pores of the osteoconductive material have adsorbed therein a biocompatible material. In specific embodiments, the composition is dehydrated and can be re-hydrated for use as described herein. The presence of the biocompatible material in the pores of the osteoconductive particles can be particularly beneficial in facilitating formation of a final composition that is sufficient for the intended use. More specifically, the presence of the biocompatible material in the pores of the osteoconductive particles can prevent undesired competition during crosslinking of the polypeptide and the second polymer and ensure that sufficient binding sites on the second polymer are available for complete crosslinking with the polypeptide so as to form a useful scaffold. In the absence of the biocompatible material in the pores of the osteoconductive particles, the particles may bind a significant portion of the available sites on the second polymer so as to inhibit proper matrix scaffold formation, and the resulting material can be unfit for use and actually be cytotoxic in in vitro cell assays.

As noted above, the second polymer used in the composition can be a polysaccharide. In particular, the polysaccharide can be dextran or oxidized dextran. In other embodiments, the second polymer can be a synthetic polymer, such as polyethylene glycol. In specific embodiments, the polypeptide can comprise gelatin.

A variety of biocompatible materials can be used to be adsorbed in the pores of the osteoconductive particles. In certain embodiments, the biocompatible material can comprise a polypeptide. If desired, the polypeptide used as the biocompatible material can be the same polypeptide that is crosslinked with the second polymer. In other embodiments, the polypeptide used as the biocompatible material can be a material that is different from the polypeptide that is crosslinked with the second polymer.

The porous, osteoconductive material can be chosen for a wide variety of materials as described herein. In specific embodiments, the porous, osteoconductive material can be hydroxyapatite. The particles of the porous, osteoconductive material can be characterized in relation to certain dimensions. For example, the porous osteoconductive particles can have an average diameter of about 0.1 µm to about 2,000 µm. The particles of the porous, osteoconductive material can have a mean pore diameter (volume) of about 100 µm to about 450 µm. The particles of the porous, osteoconductive material can have a mean pore diameter (area) of about 20 µm to about 60 µm. The particles of the porous, osteoconductive material can have a porosity of about 35% or greater. The particles of the porous, osteoconductive material can have a surface area of about 1 $m^2/g$ or greater. The particles of the porous, osteoconductive material can be amorphous with interconnecting pores. The particles of the porous, osteoconductive material and the continuous matrix can be combined in specific ratios. For example, the particles of the porous, osteoconductive material and the continuous matrix can be present in a dry weight ratio of about 90:10 to about 50:50. The composition can be dehydrated, if desired, and the dehydrated composition can be provided in any desirable shape and have varying dimensions. The dehydrated composition further beneficially allows for varied uses of the material in that the clinician can manipulate pre-formed sheets or blocks (or other shapes) of the composition to form a desired size of shape material for us in a bone filling procedure.

In addition to the foregoing, the compositions of the present disclosure can include one or more additional components. In some embodiments, the composition further can comprise a scaffolding reagent. For example, the scaffolding reagent can be selected from the group consisting of polar amino acids, divalent cation chelators, and combinations thereof. In other embodiments, the composition further can comprise a buffer. In additional embodiments, the composition further can comprise an osteoinductive material. For example, the osteoinductive material can comprise bone marrow aspirates.

In specific embodiments, the composition can comprise a continuous matrix formed of gelatin crosslinked with dextran; and particles of a porous, calcium phosphate material dispersed in the continuous matrix; wherein the pores of the calcium phosphate material have adsorbed therein a content of gelatin; and wherein the composition is dehydrated.

The disclosure further provides methods of preparing a bone filler composition. In certain embodiments, the method comprises: combining particles of a porous, osteoconductive material with a solution of a polypeptide to form a slurry; and adding to the slurry a second polymer under conditions such that the polypeptide crosslinks with the second polymer to form a continuous matrix having the particles of the osteoconductive material dispersed therein. Preferably, before said adding step, at least a portion of the pores in the particles of the osteoconductive material have a biocompatible material adsorbed therein. The biocompatible material can be as otherwise described herein. Likewise, the materials used in preparing the composition can be as otherwise described herein.

In some embodiments, the second polymer can be at least partially solubilized prior to be added to the polypeptide. The method also can comprise adding a scaffolding reagent to the composition, adding a buffer to the composition, adding an osmolality adjustment agent to the composition, and/or adding an osteoinductive material to the composition. If desired, such additives may be added to the polypeptide solution before, during, or after combination with the osteoconductive particles or can be added to a solution of the second polymer. The particles of the porous, osteoconductive material, the polypeptide, and the second polymer can be combined such that the particles and the continuous matrix are present in a dry weight ratio of about 90:10 to about 50:50. The methods further can comprise dehydrating the composition. Optionally, the methods can comprise shaping the dehydrated composition—e.g., into particles, strips, plugs, cylinders, and the like.

Mixing of the materials used to form the composition may be carried out at a temperature elevated above ambient, such as about 30° C. or greater, and may be carried out for a defined time. Dehydration of the composition preferably is carried out to form a composition having a residual moisture content, an average porosity, and a median pore diameter as otherwise described herein.

The disclosure beneficially provides methods of promoting growth of connective tissue, particularly bone, through use of the composition described herein. In certain embodiments, the disclosure thus comprises methods of regenerating bone. For example, such method can comprise applying to a bone void a composition comprising a continuous matrix formed of a polypeptide crosslinked with a second polymer and particles of a porous, osteoconductive material dispersed in the continuous matrix. Moreover, the pores of the osteoconductive material can have adsorbed therein a biocompatible material. Further, after application, the composition is preferably in a hydrated form. In certain embodiments, the composition can be in a dehydrated state, and the method can comprise at least partially hydrating the composition before applying the composition. In particular, hydrating can comprise combining bone marrow aspirates with the dehydrated composition. More specifically, the composition may be partially or completely hydrated prior to administration or may be partially or completely hydrated after the dehydrated material is applied to the bone void. Such methods of treatment can be applied to any area of the body where bone growth is desired and, more particularly, to spinal treatments.

In further embodiments, the present disclosure provides various articles of manufacture. For example, the disclosure can relate to a kit comprising one or more containers containing a composition comprising a continuous matrix formed of a polypeptide crosslinked with a second polymer and particles of a porous, osteoconductive material dispersed in the continuous matrix. Preferably, the pores of the osteoconductive material can have adsorbed therein a biocompatible material. Such kits further can comprise an instruction set directed to a health care provider describing steps for administering the composition to a bone void in an amount effective for regenerating bone in the void. The composition in the kit particularly can be in a dehydrated form, and the instruction set further can describes steps for rehydrating the composition. For example, the instruction set can describe combining the composition with bone marrow aspirates. If desired, the kit further may include tools useful for shaping the dehydrated composition and/or the hydrated composition. Likewise, the kit further may include fluids useful in rehydration of the composition, such as a buffer solution.

DETAILED DESCRIPTION OF THE DISCLOSURE

The present disclosure now will be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure provides compositions that are particularly useful as bone void fillers. The composition, however, is not intended to be limited to such use. Rather, the disclosure is intended to encompass a variety of uses that may be envisioned with the knowledge of the present disclosure.

The present composition generally comprises, as one component thereof, particles of a porous, osteoconductive material. Preferably, such particles are dispersed in a continuous matrix, as further described below. The osteoconductive material may comprise any material that facilitates in-growth of bone to the area occupied by the material. In some embodiments, the osteoconductive material may comprise a material that facilitates blood vessel incursion and new bone formation into a defined passive trellis structure. More particularly, the osteoconductive material can be a calcium phosphate material, such as monocalcium phosphate, tricalcium phosphate, hydroxyapatite, coralline hydroxyapatite, and hydrates thereof (e.g., monocalcium phosphate monohydrate and dicalcium phosphate dihydrate). Biphasic calcium phosphate materials particularly may be used. For example, combinations of hydroxyapatite and tricalcium phosphate can be used in ratios of about 90:10 to about 10:90, about 80:20 to about 50:50, or about 70:30 to about 60:40.

As further, non-limiting examples, the following osteoconductive materials may be used: calcium sulfate, calcium aluminate, alumina, zirconia, aluminum silicates, polypropylene fumarate, bioactive glass, porous titanium, porous nickel-titanium alloy, porous tantalum, sintered cobalt-chrome beads, autologous bone, allogenic bone, xenogenic bone, coralline, and derivates or combinations thereof, or other biologically produced composite materials containing calcium or hydroxyapatite structural elements.

When calcium phosphate materials are used, it can be beneficial to provide the materials with a defined calcium to phosphate ratio. The calcium to phosphate ratio can be about 1 or greater but less than about 5. In specific embodiments, for example, the ratio of calcium to phosphate can be about 1 to about 2.5, about 1.2 to about 2.3, or about 1.4 to about 2.1.

The osteoconductive material may particularly be characterized in relation to the particle size of the material. In some embodiments, average particle diameter can be about 1 μm to about 3,000 μm, about 2μm to about 2,000 μm, about 5 μm to about 1,000 μm, about 10 μm to about 850 μm, or about 50 μm to about 500 μm. More particularly, particle size distribution may be such that about 80% of the particles have a diameter of about 100 μm to about 1,000 μm, about 200 μm to about 850 μm, or about 250 μm to about 750 μm.

The osteoconductive material further may be characterized in relation to the porosity and/or the surface area of the particles. For example, the particles can have a mean pore diameter (volume) of about 100 μm to about 450 μm, about 150 μm to about 400 μm, or about 200 μm to about 300 μm, and the particles can have a mean pore diameter (area) of about 20 μm to about 60 μm, about 25 μm to about 55 μm, or about 30 μm to about 50 μm. The average pore diameter (calculated as 4× volume/area) can be about 50 μm to about 150 μm, about 60 μm to about 145 μm, or about 70 μm to about 120 μm. The particles also can be characterized in relation to comprising macropores (e.g., pores having a size of about 100 μm to about 3,000 μm or about 200 μm to about 2,000 μm), micropores (e.g., pores having a size of about 1 μm to a size less than about 100 μm or about 5 μm to about 90 μm), and nanopores (e.g., pores having a size of about 0.01 μm to a size less than about 1μm or about 0.05 μm to about 0.9 μm). The particles specifically can have a porosity of about 35% or greater or, more particularly, of about 35% to about 70%, about 40% to about 65%, or about 45% to about 60%. Particle surface area preferably can be about 1 $m^2/g$ or greater, about 10 $m^2/g$ or greater, about 30 $m^2/g$ or greater, or about 50 $m^2/g$ or greater. More particularly, particle surface area can be about 20 $m^2/g$ to about 120 $m^2/g$, about 40 $m^2/g$ to about 110 $m^2/g$, or about 50 $m^2/g$ to about 100 $m^2/g$. In specific embodiments, the particles may comprise materials such that the particles are amorphous with interconnecting pores of sizes and porosity as described above.

The porous osteoconductive particles can be characterized in relation to the extensive microporosity, microporosity, and/or nanoporosity of the material that can play a key role in adsorption of other materials of the composition, as discussed further herein. As noted above, each particle can be characterized in relation to its macroporosity as well as its microporosity and nanoporosity, which can be more extensive. It is believed that the interconnected porosity can particularly drive adsorption, and this can be seen, for example, in embodiments wherein particles have an interconnected network of individual pores of a size that is about 50 μm or less, about 25 μm or less, or about 10 μm or less.

Although the osteoconductive materials used in the present disclosure may be discussed in terms of being particles, the materials should not be viewed as necessarily being limited to a specific shape. Rather, the term particle is meant to relay the nature of the material as being provided as a plurality of small, discrete members. For example, substantially rod-shaped members can be used, and such members can also be compressed if desired.

As noted above, the porous, osteoconductive particles used in the present composition can be dispersed or otherwise distributed throughout a continuous matrix that is formed of a polypeptide crosslinked with a second polymer. The crosslinked materials may form a hydrogel matrix that is stabilized or stable in that the hydrogel may be characterized as being water-swellable, poorly soluble, and/or a solid or semi-solid material at physiological temperature (i.e., about 37° C.) and in physiological fluids (e.g., aqueous body fluids having a physiological pH of about 7.4). Such hydrogel matrix beneficially may remain present in a host for a sufficient time to achieve an intended response.

The polypeptide used in forming the crosslinked matrix may comprise any tissue-derived or synthetically produced polypeptide, such as collagens or collagen-derived gelatins. In specific embodiments, collagen-derived gelatin can be a preferred polypeptide. Further embodiments, however, may comprise other gelatin-like components characterized by a backbone comprised of sequences of amino acids having polar groups that are capable of interacting with other molecules, particularly so as to form covalent bonds. For example, keratin, decorin, aggrecan, glycoproteins (including proteoglycans), and the like could be used to produce the polypeptide component. In one embodiment, the polypeptide component can be porcine gelatin from partially hydrolyzed collagen derived from skin tissue. Polypeptides derived from other types of tissue could also be used. Examples include, but are not limited to, tissue extracts from arteries, vocal chords, pleura, trachea, bronchi, pulmonary alveolar septa, ligaments, auricular cartilage or abdominal fascia; the reticular network of the liver; the basement membrane of the kidney; or the neurilemma, arachnoid, dura mater or pia mater of the nervous system.

Still further materials that may be useful as a polypeptide material according to the disclosure are described in U.S. Pat. Nos. 6,303,765, 6,284,284, 6,264,992, and 4,829,000, the disclosures of which are incorporated herein by reference in their entireties. The polypeptide specifically can have a molecular weight of about 3,000 to about 3,000,000 Da, about 10,000 to about 750,000 Da, or about 30,000 to about 300,000 Da.

The polypeptide preferably can be present at a concentration of about 25 mg/g or greater. In other embodiments, the polypeptide concentration can be about 25 mg/g to about 600 mg/g, about 30 mg/g to about 500 mg/g, or about 40 mg/g to about 400 mg/g on a dry weight basis.

The polypeptide component of the matrix may be referred to as the first polymer used in the composition. Preferably, the composition includes a second polymer that includes binding sites for crosslinking with the polypeptide. Such binding sites may be inherent to the second polymer, may be formed by pretreatment of the second polymer to convert non-functional groups into binding sites (e.g., oxidizing the second polymer), or may be present as groups added to the second polymer to form a functionalized polymer. The second polymer used in forming the crosslinked matrix thus may encompass a broad range of materials.

In some embodiments, the second polymer may be a polysaccharide and may comprise any polysaccharide consisting of more than about 10 monosaccharide residues joined to each other by glycosidic linkages (including polysaccharides formed of the same monosaccharide residues or various monosaccharide residues or derivatives of monosaccharide residues). In specific embodiments, dextran (or a derivative thereof) can be a particularly preferred polysaccharide. In further embodiments, polysaccharides useful according to the disclosure can include heparin, heparan, hyaluronic acid, alginate, agarose, carrageenan, amylopectin, amylose, glycogen, starch, cellulose, chitin, chitosan, and various sulfated polysaccharides such as heparan sulfate, chondroitin sulfate, dextran sulfate, dermatan sulfate, and keratan sulfate. As discussed further below, derivatives of the polysaccharides, such as, for example, oxidized dextran, can be particularly useful. The polysaccharide can have a molecular weight of about 2,000 to about 8,000,000 Da, about 10,000 to about 2,000,000, or about 20,000 to about 1,000,000 Da.

In other embodiments, the second polymer may be a synthetic polymer. Such synthetic polymers preferably can be hydrophilic and are biocompatible. Non-limiting examples of synthetic polymers useful herein include polyethylene glycol (PEG), polymethylene glycol, polytrimethylene glycols, polyvinylpyrrolidones, polyoxyethylene-polyoxypropylene block polymers, and copolymers, and derivatives of the foregoing. The synthetic polymers can be linear or multiply branched. Suitable synthetic polymers preferably can be functionalized with one or more functional groups, particularly groups suitable for crosslinking with a polypeptide. The synthetic polymers can be mono-, di-, and multifunctionally activated polymers, such as functionally activated polyethylene glycols. Exemplary functional groups that may be present on the synthetic polymer include acrylate groups, succinimidyl groups, aldehyde groups, benzotriazloe groups, and isocyanate groups. Useful synthetic polymers may have an average molecular weight of about 3,000 Da to about 1,000,000, about 4,000 Da to about 500,000 Da, or about 5,000 Da to about 100,000 Da. Unless otherwise noted, molecular weight is expressed as number average molecular weight ($M_n$), which can be defined by the following formula:

$$\frac{\sum NiMi}{\sum Ni},$$

wherein Ni is the number of polymer molecules (or the number of moles of those molecules) having molecular weight Mi.

The second polymer preferably can be present at a concentration of about 10 mg/g or greater. In specific embodiments, the second polymer can be present at a concentration of about 10 mg/g to about 500 mg/g, about 15 mg/g to about 400 mg/g, or about 20 mg/g to about 300 mg/g on a dry weight basis.

The continuous matrix may be formed by covalently crosslinking the polypeptide with the second polymer. Covalent bonding may proceed via reaction of functional groups on the polypeptide with functional groups on the second polymer. In other embodiments, for example, crosslinking can proceed via reaction of a bifunctional crosslinker molecule with both the polypeptide and the second polymer. For example, one method of crosslinking gelatin and dextran is to modify the dextran, such as by oxidation, in order to form functional groups suitable for covalent attachment to the gelatin. One known reaction for oxidizing polysaccharides is periodate oxidation, such as described generally in *Affinity Chromatography: A Practical Approach*, Dean, et al., IRL Press, 1985 ISBN0-904147-71-1, which is incorporated by reference in its entirety. The oxidation of dextran by the use of periodate-based chemistry is described in U.S. Pat. No. 6,011,008, which is herein incorporated by reference in its entirety. Using such methods, a hydrogel matrix useful according to the present disclosure may be prepared at temperatures of about 30° C. to about 90° C., about 40° C. to about 80° C., or about 50° C. to about 70° C. Additionally, the hydrogels can be prepared at a pH range of from about 3 to about 11, about 4 to about 10, about 5 to about 9, about 6 to about 8, or about 7 to about 7.6.

In other embodiments, the crosslinked continuous matrix may be prepared using a multifunctional crosslinking agent as a reactive moiety that covalently links the polypeptide with the second polymer. Exemplary crosslinking agents may include glutaraldehyde, epoxides (e.g., bis-oxiranes), oxidized dextran, p-azidobenzoyl hydrazide, N[α-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl propionate, disuccinimidyl suberate, 1-ethyl-3-[3-dimethylaminopropyl]carbodiimide hydrochloride, and other bifunctional crosslinking reagents known to those skilled in the art. Alternatively, photo-activated crosslinking may be applied.

The hydrogel used as the continuous matrix may additionally contain one or more scaffolding reagents that can be characterized as enhancing formation of the crosslinked polypeptide/second polymer scaffold or matrix and/or as stabilizing the matrix. The scaffolding reagent can include any compound, especially polar compounds, that, when incorporated into the crosslinked matrix, enhance the matrix by providing further stability or functional advantages. In certain embodiments, the matrix can comprise an amount of polar amino acids, which are commonly defined to include tyrosine, cysteine, serine, threonine, asparagine, glutamine, asparatic acid, glutamic acid, arginine, lysine, and histidine. In some embodiments, the amino acids specifically can be selected from the group consisting of cysteine, arginine, lysine, histidine, glutamic acid, aspartic acid and mixtures thereof, or derivatives or analogues thereof. Additionally, one or more divalent cation chelators may be used as a scaffolding reagent. Such reagents can function to increase the rigidity of the matrix by forming coordinated complexes with any divalent metal ions present. One example of a divalent cation chelator that can be used in the present disclosure is ethylenediaminetetraacetic acid (EDTA) or a salt thereof. In further embodiments, useful scaffolding reagents may comprise metal salts, such as zinc sulfate.

When scaffolding reagents are present, the scaffolding reagents can be present in a concentration of about 0.05 mg/g to about 40 mg/g, about 0.1 mg/g to about 30 mg/g, or about 0.25 mg/g to about 20 mg/g on a dry weight basis.

The hydrogel matrix may include a physiologically compatible buffer. One example is Medium 199, a common nutrient solution used for in vitro culture of various mammalian cell types (available commercially from Sigma Chemical Company, St. Louis, Mo.), which can be further supplemented with additives and additional amounts of some medium components, such as supplemental amounts of polar amino acids as described above. Other examples of suitable buffers include phosphate buffered saline (for example, comprising 137 mM sodium chloride, 10 mM sodium phosphate, and 2.7 mM potassium chloride and having a pH of 7.4) and sodium acetate. Still further pH buffers may be used in the composition.

The hydrogel matrix also may include one or more osmolality adjustment agents. For example, metal salts, such as sodium chloride, can be used. The osmolality adjustment agents can be present in a concentration of about 0.01 mg/g to about 5 mg/g, about 0.25 mg/g to about 4 mg/g, or about 0.05 mg/g to about 2 mg/g on a dry weight basis.

In addition to the osteoconductive particles, the compositions of the present disclosure can include one or more further materials that can be useful when applied to bone or bone voids. For example, the disclosed compositions can comprise one or more osteoinductive materials. Non-limiting examples of osteoinductive materials that can be included in the disclosed compositions include bone morphogenetic proteins (BMPs), transforming growth factors (TGFs), fibroblast growth factors (FGFs), insulin-like growth factors (IGFs), platelet-derived growth factors (PDGFs), epidermal growth factors (EGFs), vascular endothelial growth factors (VEGFs), vascular permeability factors (VPFs), cell adhesion molecules (CAMs), platelet-rich plasma, natural or synthetic peptides, bone marrow aspirates, and combinations thereof.

Compositions according to the present disclosure further can comprise one or more medicaments useful for treating patients having connective tissue damage or in need of connective tissue regeneration, particularly bone regeneration. The medicament can be any medicament useful in facilitating the healing and regenerative process. Such medicaments useful according to the disclosure can include, but are not limited to, antivirals, antibacterials, anti-inflammatories, immunosuppressants, analgesics, anticoagulants, wound healing promotion agents, and combinations thereof.

If desired, compositions according to the present disclosure also can comprise cells. For example, stem or progenitor cells, such as ADAS cells, can be used in the presently disclosed compositions. In particular, useful cells can include any cells that are useful for differentiating into adipogenic, osteogenic, chondrogenic, and/or myogenic lineages.

Further examples regarding preparation of a crosslinked hydrogel matrix, materials for use in preparing a crosslinked hydrogel matrix, and characteristics thereof can be found in U.S. Pat. No. 8,053,423, the disclosure of which is incorporated herein by reference in its entirety. Although the present composition comprises particularly a crosslinked matrix, the disclosure does not necessarily exclude non-crosslinked hydrogels, such as those described in U.S. Pat. Nos. 6,231,881 and 6,261,587, the disclosures of which are incorporated herein by reference in their entireties. Even further hydrogels that may be added to the composition of the present disclosure or may be modified for crosslinking and use according to the present disclosure are described in U.S. Pat. Nos. 5,614,205, 5,824,331, 5,776,324, 5,908,633, 5,922,339, 6,352,707, 6,713,079, and 7,700,660, the disclosures of which are incorporated herein by reference in their entireties.

The composition of the disclosure preferably is formed via a method of preparation that does not negatively impact performance properties of the components of the composition. For example, it has been found that the order of addition of components in the process of forming the composition can have a significant impact on the clinical usefulness of the final composition. Specifically, it was found that when the composition was prepared by combining all components of the composition concurrently (e.g., combining the polypeptide, the polysaccharide, the porous, osteoconductive particles, any scaffolding reagents, and any crosslinking agents), the final product was partially soluble in warm water and was surprisingly cytotoxic in in vitro cell culture assays. Similar results were obtained in tests where the polysaccharide and the porous osteoconductive particles were premixed before addition of the polypeptide component.

On the other hand, it was found that premixing of the polypeptide and the porous osteoconductive particles before addition of the polysaccharide did not lead to the unacceptable results noted above but rather provided an end product highly useful in bone regeneration, as otherwise discussed herein. While not wishing to be bound by theory, it is believed that the high surface area of the porous osteoconductive particles can cause the particles to competitively bind the polysaccharide component to the detriment of the overall composition by preventing necessary crosslinking between the polypeptide and the polysaccharide.

It has been found according to the present disclosure, however, that pre-loading of the porous osteoconductive particles with a biocompatible material prior to contact with the polysaccharide component of the composition (or other second polymer) can reduce or eliminate the competitive binding and facilitate formation of the useful end product. In specific embodiments, the biocompatible material with which the porous osteoconductive particles are pre-loaded can be a polypeptide. Moreover, the polypeptide used to pre-load the porous osteoconductive particles can be the same polypeptide material used in forming the final composition. For example, the porous osteoconductive particles can be added to a solution of the polypeptide material under conditions sufficient to allow fragments of the polypeptide to penetrate the porous networks of the particles and become adsorbed therein. Thus, the biocompatible material (e.g., a polypeptide) can be attached to a surface of the particles, including surfaces within the particle pores. More specifically, the biocompatible material can be at least partially filling the pores of the porous osteoconductive particles.

While it can be beneficial for the biocompatible material used in pre-loading the porous osteoconductive particles to be the same polypeptide used in forming the final composition, the disclosure is not necessarily limited to such embodiments. Rather, other polypeptides (such as those disclosed herein) could be used as the pre-loading material. Further, other beneficial materials could be used as the pre-loading component, such as medicaments, growth factors, cells, or the like. Moreover, the porous osteoconductive particles may be pre-loaded with a material that is biocompatible yet is relatively inert in relation to the crosslinking of the composition or the use of the composition in bone regeneration. While other materials may be used in pre-loading the porous osteoconductive particles, it still can be beneficial according to the present disclosure to pre-mix the porous osteoconductive particles with a solution of the polypeptide material prior to addition of the polysaccharide material or other second polymer.

When using the polypeptide of the composition as the pre-loading material, it can be beneficial to mix the porous osteoconductive particles with a solution of the polypeptide at a temperature greater than ambient for a defined period of time. For example, mixing may be carried out at a temperature of about 30° C. to about 90° C., about 40° C. to about 80° C., or about 50° C. to about 70° C. Mixing of the polypeptide solution and the porous osteoconductive particles can be carried out for a time of about 5 minutes or greater, about 10 minutes or greater, about 20 minutes or greater, about 30 minutes or greater, or about 1 hour or greater. In other embodiments, mixing can be carried out for a time of about 5 minutes to about 8 hours, about 10 minutes to about 4 hours, or about 20 minutes to about 2 hours. In certain embodiments, any scaffolding reagents and other additives to be added to the composition (e.g., polar amino acids, EDTA, zinc sulfate, pH adjustors) can be combined with the polypeptide solution before or after addition of the porous osteoconductive particles.

Once the polypeptide material and the porous osteoconductive particles have been combined, the second polymer can be added, preferably with mixing. The second polymer may be functionalized (e.g., dextran that has been oxidized) to facilitate crosslinking, or a suitable crosslinking agent may be added to the solution containing the polypeptide, may be added to the solution containing the polysaccharide, or may be added to the solution containing both the polypeptide and the polysaccharide. The polypeptide and the second polymer thus can crosslink to from a continuous matrix. The composition may be cured for a time of up to about 24 hours, up to about 18 hours, or up to about 12 hours to allow for completion of crosslinking. Crosslinking may be allowed to occur for a time of about 30 seconds to about 24 hours, about 5 minutes to about 18 hours, or about 30 minutes to about 12 hours. Moreover, crosslinking may be carried out at an elevated temperature, such as described above or, alternately, after mixing of the all materials, the composition may be cooled to ambient or below to permit crosslinking to move to completion.

In some embodiments, it can be beneficial to mix the solution during crosslinking so as to entrap air in the matrix and provide a desired level of porosity to the structure. Desired porosity also may be achieved through introduction of solid or hollow soluble materials, as well as other pore forming agents, into the solution before or during crosslinking The crosslinked matrix with the porous osteoconductive particles dispersed therein may be used immediately in filling bone voids or in other methods of regenerating connective tissue, particularly bone. The crosslinked matrix also may be shaped, such as by casting while crosslinking occurs. The non-crosslinked or partially crosslinked liquid composition may be poured into molds providing a uniform dimension useful in a commercial form or useful in specific application. The crosslinked compositions thus can take on the shape and dimensions of the molds used.

In some embodiments, the composition of the continuous, crosslinked matrix with the porous osteoconductive particles dispersed therein can be dehydrated. This can provide the composition in a stable, storage-ready form that can be used by clinicians in a variety of settings and applications. In specific embodiments, the crosslinked continuous matrix with the porous osteoconductive particles dispersed therein can be dehydrated to include 15% or less, 12% or less, 10% or less, or 6% or less moisture by weight. As noted above, however, dehydration is not necessarily required, and the fully formed and hydrated product can be used immediately or can be prepared for use at a later date. Thus, a prepared, hydrated composition can be prepared by the end user or can be taken up for use by the end user in the prepared, hydrated form.

When dehydration is used, the dehydration can be carried out using any method sufficient to provide the end product with the desired characteristics as discussed herein. For example, lyophilization may be used. In such embodiments, the composition may be pre-frozen to a first temperature so as to maintain desired structures and dimensions of the composition. Thereafter, the composition may be lyophilized.

The pre-freezing method and the final frozen product temperature can both affect the ability to successfully freeze dry the material. Rapid cooling forms small ice crystals. While small crystals are useful in preserving structure, they result in a product that is more difficult to freeze dry. Slower cooling results in larger ice crystals and produces less restrictive channels in the matrix during the drying process. Pre-freezing to temperatures below the eutectic temperature, or glass transition temperature, is beneficial for complete drying of the composition. Inadequate freezing may produce small pockets of unfrozen material remaining in the product which may expand and compromise the structural stability of the freeze dried product. After pre-freezing, temperatures can be applied to effect sublimation of ice present in the material. Thereafter, further dehydration may be carried out to achieve the desired moisture content and may be performed at a temperature that is greater than in the sublimation step.

The dehydrated composition can be substantially in the form a single mass. The single mass can be customized for specific uses as desired. Advantageously, the dehydrated composition can be shaped. For example, the dehydrated composition can be sliced into wafer-like slices of varying dimensions. The dehydrated composition also can be ground or otherwise processed to be in a particulate form and thus be shaped as particles. The dehydrated composition also can be cut to various shapes and dimensions for specified uses, such as preformed plugs for use in bone repair. For example, the dehydrated composition can be formed to a standardized shape and size and packaged for various uses. Such shaping can be carried out by a manufacturer and/or an end-user. For example, the dehydrated composition can be provided in the form of strips that are substantially flattened having a thickness that is less than the length and width thereof. Varying shapes and sizes of the shaped, dehydrated composition are encompassed by the present disclosure. In a further embodiment, the dehydrated composition can be shaped around a central mandrel to form porous tubes useful for tissue regenerative guidance conduits. These can be wrapped around specific sites which may require or benefit from guided tissue regeneration. Dehydrated compositions can also be partially rehydrated to form putties and pastes appropriate for filling bony voids. The dehydrated composition, when re-hydrated, can retain its regenerative properties as described herein and can be used according to the methods of the disclosure as effectively as a freshly prepared composition. The re-hydration of the composition can be performed according to various methods, all of which are encompassed by the present disclosure. In one embodiment, the dehydrated composition can be re-hydrated prior to use, such as by contacting with water, a physiologically compatible buffer solution, such as Medium 199, or with bone marrow aspirates. In another embodiment, the dehydrated composition can be placed in the site in need of regeneration and then contacted with re-hydrating fluids, such as water or, physiologically compatible buffer solution, or bone marrow aspirates. In still another embodiment, the dehydrated composition can be placed in the site in need of regeneration and then re-hydrated through contact with natural body fluids. Further details regarding dehydrations methods that can be useful herein are discussed in U.S. Patent Pub. No. 2005/0118230 and U.S. Pat. No. 7,695,736, the disclosures of which are incorporated herein by reference in their entireties.

Although the present composition may be discussed in terms of being in a crosslinked form at the time of administration, the use of the composition is not so limited. The composition can be provided in a form that is adapted for in-situ crosslinking. For example, the composition can be provided in the form of a kit wherein the individual components of the composition can be combined in a variety of fashions such that the polypeptide material and the second polymer material are separated. All components can be provided in a dried form with suitable instructions for the order of combination of materials for hydration and crosslinking to form the continuous matrix. If desired, the instructions can include direction for pre-mixing the polypeptide material, separately pre-mixing the second polymer material, and combining the two mixtures immediately prior to application or at the time of application so that crosslinking occurs at the administration site. Similarly, the hydrated materials can be provided in a container whereby the hydrated materials are separated but can be intermixed in the container (e.g., having a separating membrane that can be broken to allow intermixing) or can be intermixed upon dispensing from the container (e.g., in a multi-barrel syringe from which the desired content of hydrated polypeptide and hydrated second polymer can be dispensed). In any event, it is understood that the composition of the preset disclosure is not limited to being fully crosslinked at the time of administration but can be partially or completely crosslinked in-situ.

A dehydrated composition may be characterized in relation to various physical properties, particularly porosity. The crosslinked continuous matrix with the porous osteoconductive particles dispersed therein specifically may be characterized as having interconnecting pores with a median pore diameter of about 102 μm (pore sizes ranging up to about 820 μm) and an average porosity of about 85%. In certain embodiments, the matrix can have a porosity of about 25% or greater, about 50% or greater, or about 75% or greater. More particularly, the average porosity can be about 50% to about 95%, about 60% to about 92%, or about 70% to about 90%. Median pore diameter (volume) of the matrix can be about 25 μm or greater, about 50 μm or greater, or about 75 μm or greater. More particularly, the matrix can have a median pore diameter (volume) of about 25 μm to about 200 μm, about 50 μm to about 175 μm, or about 75 μm to about 150 μm. Median pore diameter (area) of the matrix can be about 0.005 μm to about 1 μm, about 0.008 μm to about 0.5 or about 0.01 μm to about 0.1 μm. Average pore diameter of the matrix (calculated as 4× volume/area) can be about 0.01 μm to about 2 μm, about 0.05 to about 1.5 μm, or about 0.1 μm to about 1 μm. The bulk density (measured at 0.22 psia) of the dehydrated crosslinked continuous matrix with the porous osteoconductive particles dispersed therein can be about 5 g/mL or less, about 2 g/mL or less, or about 1 g/mL or less. More specifically, the bulk density can be about 0.05 g/mL to about 5 g/mL, about 0.08 g/mL to about 2 g/mL or about 0.1 g/mL to about 1 g/mL.

The dehydrated composition further can be characterized in relation to the relative amount of the components therein. Specifically, the osteoconductive particles and the crosslinked continuous matrix may be present in a defined dry weight ratio, such as about 75:25. In certain embodiments, the dry weight ratio of particles to matrix can be about 90:10 to about 50:50, about 85:15 to about 60:40, or about 80:20 to about 70:30. Useful ranges of components present in formulation for a dehydrated composition according to the present disclosure are provided in Table 1 below.

TABLE 1

| Component | Concentration (mg/g) |
|---|---|
| Porous Osteoconductive Particles (e.g., hydroxyapatite) | 500-900 |
| Carrier | |
| Polypeptide (e.g., gelatin - Type A porcine skin) | 65-300 |
| Second Polymer (e.g., oxidized dextran) | 25-200 |
| Residual water | 5-30 |
| pH buffers | 3-15 |
| Scaffolding Reagents | 0.5-10 |
| Osinolality Adjustment Agent | 0.1-1 |
| Total (mg) | 1000 |

In the foregoing table, pH buffers can include, for example sodium phosphate dibasic, sodium acetate, potassium phosphate monobasic, and sodium hydroxide. Scaffolding reagents particularly can include L-Glutamic acid, monosodium salt, L-Arginine monohydrochloride, L-Lysine acetate, L-Cysteine HCl, zinc sulfate, and EDTA disodium. Sodium chloride is an exemplary osmolality adjustment agent.

The present disclosure further provides various methods of use of the described compositions. For example, the composition of the present disclosure can be for use in regenerating bone. The use can be in a mammal, particularly a human. The area of bone regeneration can be an area corresponding to a fracture. The area of bone regeneration also can be an area of bone loss. The area of bone regeneration likewise can be in or around a bone void.

In particular embodiments, the methods and use of the present disclosure can comprise administering a composition as described herein to a site in need of bone regeneration. The composition preferably is administered in a therapeutically effective amount. In particular, the amount can be a volume that is about 25% or more, about 50% or more, or about 75% or more of the volume of the bone void. In other embodiments the amount can be a volume of about 25% to about 200%, about 50% to about 150%, or about 75% to about 125% of the volume of the bone void.

In use, the composition of the present disclosure can be in a dehydrated form. Thus, the methods and use of the present disclosure can comprise at least partially re-hydrating the composition. Such re-hydration can occur before, during, or after administration of the composition. Re-hydration can be carried out using any suitable fluid, including water, biologically compatible buffer solutions, and bone marrow aspirates.

The present disclosure also encompasses kits comprising the described composition. The kits further can include an instruction set for the use of the composition. The instruction set particularly can be directed to a health care provider. The instruction set can describe steps for administering the composition to a bone void in an amount effective for regenerating bone in the void. In embodiments wherein the composition is in a dehydrated form, the instruction set further can describe steps for rehydrating the composition. In particular, the instruction set can describe combining the composition with bone marrow aspirates.

EXPERIMENTAL

Performance Testing

Animal

The radiographic, biomechanical, histological and other characteristics of example embodiments of compositions according to the present disclosure (labeled as "NB3D") were compared in a rabbit single-level posterolateral fusion model to those of the known material Vitoss BA Bioactive Bone Graft Substitute and to autograft (positive control).

The composition of the present disclosure was formed of hydroxyapatite, gelatin, dextran, sodium phosphate dibasic, L-Glutamic acid, L-Arginine, EDTA, L-Lysine, sodium chloride, potassium phosphate, L-Cysteine, zinc sulfate, and residual water. To prepare the composition, a stock 24% gelatin solution prepared in a physiologic buffer containing polar amino acids was warmed in a temperature controlled bead bath at 50° C. (±5° C.). Osteoconductive granules were weighed out, mixed with an approximately equal mass of water, and set aside. The moistened osteoconductive granules were added to the warmed gelatin solution and mixed to form a uniform slurry at 50° C. (±5° C.). The osteoconductive granules, gelatin, and a solution of oxidized dextran were combined at a ratio of approximately 1:1:1 and mixed until homogeneous. Air can be entrapped in the mixture to create a porous matrix while crosslinking of the gelatin and oxidized dextran occurs. A so-formed foam was allowed to set further at room temperature before being transferred to a curing chamber held at 5° C. (+3° C.) for 6 to 18 hours. The cured foam was removed from its mold, and transferred to a washing vessel containing an equal volume of purified water. The foams were washed for 6 to 18 hours at 5° C. (±3° C.) to remove any residual, non-crosslinked oxidized dextran. The washed foams were placed in a freeze-drying tray, and placed in a freeze-dryer with a pre-programmed cycle of temperatures and pressures under computer control. Freeze-drying typically was completed within 2 to 5 days. At the end of the freeze-drying cycle, the dehydrated foams were removed from the freeze-dryer, inspected for defects or voids, gamma sterilized, and set aside for use in the testing.

The presently disclosed and comparative test materials were each, separately combined with bone marrow aspirate ("BMA"). The study was conducted at the Surgical and Orthopaedic Research Laboratories of the University of New South Wales. The graft material was placed adjacent to the vertebral body as well as between the transverse processes (10 mm lateral to the midline) and was performed in 56 six month old rabbits. A pneumatic burr (Midas Rex with an M8 burr) was used for decortication. Three cc of each material were implanted in each level (1.5 cc per side) to control for volume of graft material placed into each animal. The fascial incisions were closed with 3-0 absorbable suture and the skin approximated using 3-0 suture. Animals were euthanized at 6 and 12 weeks for macroscopic inspection, radiographic grading using a modified Lenke scale, micro-computed tomography, mechanical testing, paraffin histology, immunohistochemistry for IL-6, MMP-1, MMP-13 and Cathepsin K, PMMA histology and histomorphometry. The study design is outlined in Table 2 below.

TABLE 2

| Group | Treatment | Baseline* | Sacrifice Time Points 6 weeks | 12 weeks | Total Animals |
|---|---|---|---|---|---|
| 1 | NB3D (with BMA and autograft) | 1 | 8 | 8 | 17 |
| 2 | NB3D (with BMA) | 1 | 0 | 8 | 9 |
| 3 | Vitoss BA Bioactive Bone Graft Substitute (with BMA) | 1 | 8 | 8 | 17 |
| 4 | Autograft with BMA | 1 | 8 | 8 | 17 |

*Baseline animals for histomorphometry only

NB3D was provided to the test facility as individually packaged sterile 1.5 cc strips. For each animal, two NB3D graft strips (1.5 cc each) were immersed in 3 cc of BMA for 5 minutes to hydrate. For treatment Group 1, 3 cc of iliac crest autograft was divided into equal 1.5 cc amounts, of which 1 cc was placed bilaterally in the right and left inter-transverse process space. From the remaining autograft, 0.5 cc was placed into each of the two hydrated NB3D graft strips, which were placed bilaterally on the decorticated transverse processes in the inter-transverse space on top of (posterior to) the 1 cc of autograft. For treatment Group 2, the NB3D material was hydrated with BMA as described above and was placed bilaterally in the inter-transverse space without autograft. For treatment Group 3, the Vitoss BA Bioactive Bone Graft Substitute was hydrated with BMA according to the product labeling. After hydration of the two grafts, 1.5 cc each were cut from the Vitoss BA, and were placed bilaterally in the inter-transverse space. For Group 4, 3 cc of iliac crest autograft was mixed with 3 cc of BMA, divided into equal amounts and placed bilaterally in the inter-transverse space.

The study evaluation endpoints and descriptions of the methods used are outlined in Table 3. Except as noted, all endpoint evaluations were performed on all animals at the 6 and 12 week time points.

TABLE 3

| Evaluation Endpoints | Description |
|---|---|
| Gross Inspection | Presence of adverse reactions upon dissection and harvest |
| Fusion by Palpation | Assess fusion rate by manual palpation of the graft site |
| Radiography | Grading of bone continuity between transverse processes |
| Micro-Computed Tomography (µCT) | Bone quality and continuity between the transverse processes in the axial, coronal, and sagittal planes; performed on 2 animals per treatment group at 6 and 12 weeks |
| Biomechanics | Tensile stiffness, peak load, energy to failure, and rigidity (manual palpation); 12 week animals |
| Histology, including decalcified (paraffin) and undecalcified (PMMA) sections | Histological appearance in implant regions adjacent to and between the transverse processes: inflammatory response and cell types; new bone formation; presence or absence of bone necrosis; and presence or extent of myelofibrosis |
| Histomorphometry (PMMA sections) | Amount of bone formation and implant resorption in regions adjacent to and between the transverse processes |
| Immunohistochemistry (paraffin sections) | Expression of MMP-1, MMP-13, IL-6 and Cathepsin K in implant regions adjacent to and between the transverse processes |
| Distant Organs | Presence or absence of gross or histologic pathology in heart, liver, kidney, lungs and spleen |

Radiographs of harvested spine segments were graded by two blinded observers for evidence of new bone formation and fusion on each side of the spine, and the amount of bone formation between the transverse processes was scored using a 5-point scale (Grade 1, new bone from 0 to 20%, and Grade 5, new bone 80% to 100%). Qualitatively the radiographs demonstrated progressive increases in radiopacity at the transverse processes and at the middle of the developing fusion for Group 1 (NB3D with BMA and autograft), Group 2 (NB3D with BMA) and Group 4 (autograft with BMA); for Group 3 (Vitoss BA) new bone formation was noted at the transverse processes but not in the middle of the fusion site. For Groups 1, 3, and 4 the mean radiographic new bone scores increased from 6 weeks to 12 weeks (Group 2 having only 12 week animals). At 12 weeks the mean radiographic new bone scores for the NB3D groups (Group 1, mean score 3.94; Group 2, mean score 3.56) compared favorably to the autograft group (Group 4, mean score 3.94) in contrast to the Vitoss BA group (Group 3, mean score 1.07).

Micro-computed tomography evaluation was consistent with the radiographic findings. At 12 weeks, micro-computed tomography demonstrated new bone formation along the transverse processes and in the middle of the fusion mass and extensive graft remodeling for Group 1 (NB3D with BMA and autograft), Group 2 (NB3D with BMA) and Group 4

(autograft with BMA); in Group 3 (Vitoss BA) new bone formation was present only on the transverse processes with minimal graft remodeling.

Fusion was manually assessed for rigidity on manual palpation and indicated comparable fusion rates in Group 1 (NB3D with BMA and autograft), Group 2 (NB3D with BMA) and Group 4 (autograft with BMA) at 43%, 50%, and 38%, respectively. None of the Group 3 (Vitoss BA) animals were judged to be fused by manual palpation.

After rigidity assessment, isolated spine segments were dissected to remove all muscle, tendon, and ligament and evaluated in biomechanical testing for peak load, stiffness, and energy to peak load. The peak load and energy were each statistically significant, and peak load was statistically significantly greater in Group 4 (autograft with BMA) as compared to Group 3 (Vitoss BA), There were no statistically significant differences between Groups 1 and 2 and 4 for these parameters.

Histologic evaluation of specimens taken at the transverse processes at 6 weeks and 12 weeks demonstrated an osteoconductive response with woven bone formation and subsequent remodeling. Histology in the middle of the fusion mass (between the transverse processes) also demonstrated an osteoconductive response with remodeling and the development of marrow spaces in Group 1 (NB3D with BMA and autograft) and Group 4 (autograft with BMA) at both 6 weeks and at 12 weeks, and in Group 2 (NB3D with BMA) at 12 weeks (not tested at 6 weeks). In Group 3 (Vitoss BA), bone formation between the transverse processes was negligible at both 6 weeks and at 12 weeks. These results were confirmed using histomorphometry (see Table 4). Due to the variability of these data, however, these differences did not reach statistical significance.

The baseline (time zero) results were 9.90±2.31% bone for Group 1 (NB3D with BMA and autograft), and 14.45±1.90% bone for Group 4 (autograft with BMA).

Immunohistologic expression of MMP-1, MMP-13, IL-6 and Cathepsin K was evaluated in Group 1 (NB3D with BMA and autograft), Group 3 (Vitoss BA) and Group 4 (autograft with BMA) at 6 weeks, and in all groups (including Group 2-NB3D with BMA) at 12 weeks. Protein expression decreased from 6 weeks to 12 weeks in all groups except for IL-6, which was expressed at similar intensity at 6 weeks and at 12 weeks in Group 3 (Vitoss BA). The expression intensity of each protein at 12 weeks was similar for Group 2 (NB3D with BMA) and Group 1 (NB3D with BMA and autograft).

Posterolateral fusion models provide rigorous testing of bone graft materials and thus provide insight into clinical performance of the materials. Graft materials must perform not only on the decorticated host bone but between the transverse process to achieve fusion between the treated levels. The composition of the present disclosure was efficacious when mixed with autograft and BMA as well as when mixed with BMA alone and provided an osteoconductive scaffold that supported new bone formation on the transverse processes as well as in the middle of the fusion mass and that remodeled with time based on all endpoints. The nano-structured hydroxyapatite material in the disclosed composition resorbed with time but had yet to completely resorb at 26 weeks. On the contrary, Vitoss BA mixed with BMA provided only negligible amounts of new bone in the middle of the fusion mass at 6, 12, and 26 weeks. The testing thus illustrated that the compositions of the present disclosure provided improved performance over another, commercially available bone void filler.

Many modifications and other embodiments will come to mind to one skilled in the art to which this disclosure pertains having the benefit of the teachings presented in the foregoing descriptions and the associated drawings. Therefore, it is to be

TABLE 4

| | Group 1 NB3D (with BMA and autograft) | | Group 2 NB3D (with BMA) | Group 3 Vitoss BA | | Group 4 Autograft with BMA | |
|---|---|---|---|---|---|---|---|
| | 6 weeks | 12 weeks | 12 weeks | 6 weeks | 12 weeks | 6 weeks | 12 weeks |
| On Transverse Processes | | | | | | | |
| Bone | 23.10 ± 6.51 | 23.10 ± 6.67 | 13.57 ± 8.97 | 12.34 ± 6.28 | 17.45 ± 4.68 | 23.92 ± 4.56 | 20.83 ± 5.74 |
| Residual Graft Material | 36.09 ± 6.33 | 37.63 ± 8.30 | 44.84 ± 9.40 | 52.01 ± 9.98 | 36.80 ± 12.73 | NA | NA |
| Middle of Fusion Mass | | | | | | | |
| Bone | 21.37 ± 8.10 | 12.40 ± 6.81 | 6.26 ± 7.26 | 0.27 ± 0.38 | 0.77 ± 1.35 | 19.97 ± 5.87 | 16.30 ± 2.95 |
| Residual Graft Material | 29.83 ± 8.00 | 33.05 ± 12.37 | 46.53 ± 19.72 | 65.72 ± 5.17 | 60.85 ± 10.32 | NA | NA |
| Total (average both sites) | | | | | | | |
| Bone | 21.97 ± 6.72 | 19.19 ± 4.74 | 10.11 ± 7.67 | 8.29 ± 4.06 | 7.77 ± 7.51 | 22.48 ± 3.05 | 19.33 ± 4.93 |
| Residual Graft Material | 32.83 ± 6.18 | 35.25 ± 7.53 | 41.85 ± 17.26 | 56.51 ± 8.37 | 51.90 ± 15.99 | NA | NA |

All values are percent, mean ± standard deviation.
NA - residual autograft bone could not be distinguished from newly formed bone.

Histomorphometric analysis of residual implant material at 12 weeks was not statistically significantly different between Group 1 and Group 2 (35.3% vs. 41.9%), and although these mean values were lower than in Group 3 (51.9%), the differences were not statistically significant ($p > 0.05$).

understood that the disclosure is not to be limited to the specific embodiments described herein and that modifications and other embodiments are intended to be included within the scope of the appended claims. Although specific terms are employed herein, they are used in a generic and descriptive sense only and not for purposes of limitation.

The invention claimed is:

1. A composition comprising:
   a continuous matrix formed of a polypeptide crosslinked with a second polymer; and
   particles of a porous, osteoconductive material dispersed in the continuous matrix;
   wherein the pores of the osteoconductive material have adsorbed therein a biocompatible material.

2. The composition according to claim 1, wherein the second polymer is a polysaccharide.

3. The composition according to claim 2, wherein the polysaccharide is dextran.

4. The composition according to claim 1, wherein the second polymer is a synthetic polymer.

5. The composition according to claim 4, wherein the synthetic polymer is a polyethylene glycol.

6. The composition according to claim 1, wherein the polypeptide comprises gelatin.

7. The composition according to claim 1, wherein the biocompatible material comprises a polypeptide.

8. The composition according to claim 7, wherein the polypeptide comprises the same polypeptide that is crosslinked with the second polymer.

9. The composition according to claim 7, wherein the polypeptide comprises a material that is different from the polypeptide that is crosslinked with the second polymer.

10. The composition according to claim 1, wherein the porous, osteoconductive material is selected from the group consisting of calcium phosphate, calcium sulfate, calcium aluminate, alumina, zirconia, aluminum silicates, polypropylene fumarate, bioactive glass, porous titanium, porous nickel-titanium alloy, porous tantalum, sintered cobalt-chrome beads, autologous bone, allogenic bone, xenogenic bone, coralline, and combinations thereof.

11. The composition according to claim 10, wherein the porous, osteoconductive material is hydroxyapatite.

12. The composition according to claim 1, wherein the particles of the porous osteoconductive material comprise macropores, micropores, and nanopores.

13. The composition according to claim 1, wherein the particles of the porous, osteoconductive material have an average diameter of about 1μm to about 3,000 μm.

14. The composition according to claim 1, wherein the particles of the porous, osteoconductive material have a mean pore diameter (volume) of about 100 μm to about 450 μm.

15. The composition according to claim 1, wherein the particles of the porous, osteoconductive material have a mean pore diameter (area) of about 20μm to about 60 μm.

16. The composition according to claim 1, wherein the particles of the porous, osteoconductive material have a porosity of about 35% or greater.

17. The composition according to claim 1, wherein the particles of the porous, osteoconductive material have a surface area of about $1m^2/g$ or greater.

18. The composition according to claim 1, wherein the particles of the porous, osteoconductive material are amorphous with interconnecting pores.

19. The composition according to claim 1, wherein the composition further comprises one or more of a scaffolding reagent, a buffer, and an osteoinductive material.

20. The composition according to claim 19, wherein the composition comprise a scaffolding reagent selected from the group consisting of polar amino acids, divalent cation chelators, and combinations thereof.

21. The composition according to claim 20, wherein the composition comprises an osteoinductive material selected from the group consisting of bone morphogenetic proteins (BMPs), transforming growth factors (TGFs), fibroblast growth factors (FGFs), insulin-like growth factors (IGFs), platelet-derived growth factors (PDGFs), epidermal growth factors (EGFs), vascular endothelial growth factors (VEGFs), vascular permeability factors (VPFs), cell adhesion molecules (CAMs), platelet-rich plasma, natural or synthetic peptides, bone marrow aspirates, and combinations thereof.

22. The composition according to claim 1, wherein the particles and the continuous matrix are present in a dry weight ratio of about 90:10 to about 50:50.

23. The composition according to claim 1, wherein the composition is dehydrated.

24. A kit comprising:
   one or more containers containing a composition comprising a continuous matrix formed of a polypeptide crosslinked with a second polymer and particles of a porous, osteoconductive material dispersed in the continuous matrix, wherein the pores of the osteoconductive material have adsorbed therein a biocompatible material; and
   an instruction set directed to a health care provider describing steps for administering the composition to a bone void in an amount effective for regenerating bone in the void.

25. A composition comprising:
   a continuous matrix formed of a polypeptide crosslinked with a second polymer; and
   particles of a porous, osteoconductive material dispersed in the continuous matrix;
   wherein the pores of the osteoconductive material have adsorbed therein a polypeptide that is the same polypeptide that is crosslinked with the second polymer.

26. A composition comprising:
   a continuous matrix formed of a polypeptide crosslinked with a second polymer; and
   particles of a porous, osteoconductive material dispersed in the continuous matrix;
   wherein the pores of the osteoconductive material have adsorbed therein a biocompatible material, and one or more of the following conditions are met:
   the particles of the porous, osteoconductive material have an average diameter of about 1μm to about 3,000 μm;
   the particles of the porous, osteoconductive material have a mean pore diameter (volume) of about 100μm to about 450 μm;
   the particles of the porous, osteoconductive material have a mean pore diameter (area) of about 20μm to about 60μm;
   the particles of the porous, osteoconductive material have a porosity of about 35% or greater;
   the particles of the porous, osteoconductive material have a surface area of about $1m^2/g$ or greater;
   the particles of the porous, osteoconductive material are amorphous with interconnecting pores;
   the particles of the porous, osteoconductive material and the continuous matrix are present in a dry weight ratio of about 90:10 to about 50:50;
   the composition is dehydrated.

* * * * *